(12) United States Patent
Bianco et al.

(10) Patent No.: US 9,011,385 B2
(45) Date of Patent: Apr. 21, 2015

(54) APPARATUS FOR THE REMOVAL OF NEEDLES OF SYRINGES

(71) Applicants: Walter Bianco, Trieste (IT); Paolo Giribona, Trieste (IT)

(72) Inventors: Walter Bianco, Trieste (IT); Paolo Giribona, Trieste (IT); Michele Minisini, Trieste (IT)

(*) Notice: Subject to any disclaimer, the term of this patent is extended or adjusted under 35 U.S.C. 154(b) by 106 days.

(21) Appl. No.: 13/760,511

(22) Filed: Feb. 6, 2013

(65) Prior Publication Data

US 2013/0150804 A1 Jun. 13, 2013

Related U.S. Application Data

(63) Continuation of application No. 13/530,165, filed on Jun. 22, 2012, now abandoned.

(30) Foreign Application Priority Data

Jun. 22, 2011 (IT) ................ BO2011A0360

(51) Int. Cl.
*A61M 5/32* (2006.01)
*A61M 5/31* (2006.01)

(52) U.S. Cl.
CPC ........... *A61M 5/3276* (2013.01); *A61M 5/3205* (2013.01); *A61M 2005/3143* (2013.01); *A61M 2005/3208* (2013.01)

(58) Field of Classification Search
CPC ................ A61M 2005/3208; A61M 5/3205; A61M 5/3276
USPC ........................................................ 604/178
See application file for complete search history.

(56) References Cited

U.S. PATENT DOCUMENTS

2005/0236289 A1* 10/2005 Tanaka et al. ................ 206/366
2005/0288636 A1* 12/2005 Cooley et al. ................ 604/187

FOREIGN PATENT DOCUMENTS

FR 2714836 7/1995
JP 8080349 3/1996

OTHER PUBLICATIONS

Italian Search Report dated Jan. 30, 2012.
U.S. Appl. No. 13/530,165, filed Jun. 22, 2012.

* cited by examiner

*Primary Examiner* — Kevin C Sirmons
*Assistant Examiner* — Deanna K Hall
(74) *Attorney, Agent, or Firm* — McCarter & English, LLP

(57) ABSTRACT

An apparatus for the removal of needles of syringes is provided with two gripping devices adapted to withhold a syringe and the respective needle, respectively, and an actuating device for moving the two gripping devices with respect to each other with a roto-translating motion about and along a longitudinal axis of the syringe in order to unscrew the needle from the syringe itself.

8 Claims, 5 Drawing Sheets

APPARATUS FOR THE REMOVAL OF NEEDLES OF SYRINGES

CROSS-REFERENCE TO RELATED APPLICATION

The present application is a continuation application claiming priority benefit to a co-pending, non-provisional patent application entitled "An Apparatus for the Removal of Needles of Syringes," which was filed on Jun. 22, 2012, and assigned U.S. Ser. No. 13/530,165. The entire content of the foregoing non-provisional application is incorporated herein by reference.

TECHNICAL FIELD

The present invention relates to an apparatus for the removal of needles of syringes.

BACKGROUND OF THE INVENTION

Each syringe comprises a containment cylinder, a plunger engaged in sliding manner in the containment cylinder and a needle screwed onto a threaded open end of the containment cylinder itself.

After the syringe has been used, the needle is unscrewed and the threaded end is sealed by means of a closing plug to allow medical personnel to handle the syringe itself safely.

In order to remove the needle from the syringe, the medical personnel inserts a syringe inside an apparatus comprising a gripping device, which has two jaws movable between a clamping position and a release position of the needle, and is moved under the bias exerted by the medical personnel through the syringe with a roto-translating movement about and along a longitudinal axis of the syringe itself.

The known apparatuses of the type described above have several drawbacks mainly deriving from the fact that the removal of the needle implies the presence and manual intervention of medical personnel, who must support the syringe and apply the thrust required to move the gripping device with the mentioned roto-translating movement.

SUMMARY OF THE INVENTION

It is the object of the present invention to provide an apparatus for the removal of needles of syringes which is free from the above-described drawbacks and which is simple and cost-effective to implement.

According to the present invention, an apparatus for the removal of needles of syringes is provided as disclosed in the appended claims.

BRIEF DESCRIPTION OF THE DRAWINGS

The present invention will now be described with reference to the accompanying drawings, which illustrate a non-limitative embodiment thereof, in which.

DETAILED DESCRIPTION OF THE INVENTION

Figure 1:
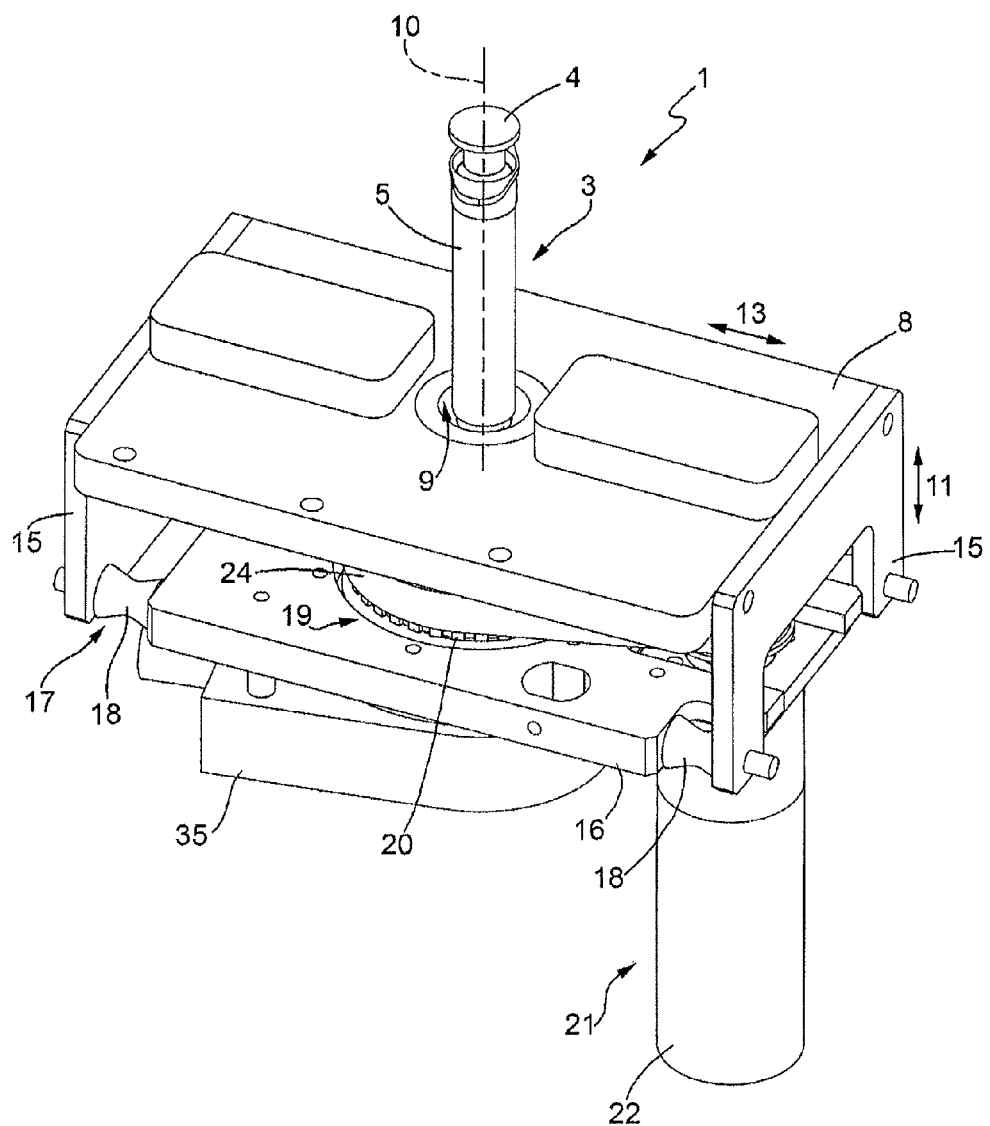
FIG. 1 is a first diagrammatic perspective view of a preferred embodiment of the apparatus of the present invention.
Figure 2:
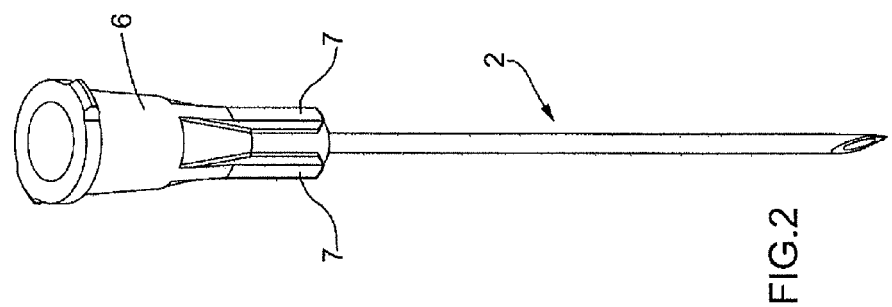
FIG. 2 is a diagrammatic perspective view of the needle of the syringe shown in FIG. 1.

With reference to FIGS. 1 and 2, numeral 1 indicates as a whole an apparatus for the removal of needles 2 of syringes 3.

Each syringe 3 comprises a plunger 4 engaged in sliding manner in a containment cylinder 5 having a threaded end (not shown) closed by a needle 2 comprising, in turn, a threaded coupling hub 6 and a plurality of projections 7 (four projections 7, in the case in point), which are uniformly distributed about a longitudinal axis of the hub 6, and radially protrude outwards from the hub 6.

Figure 3:
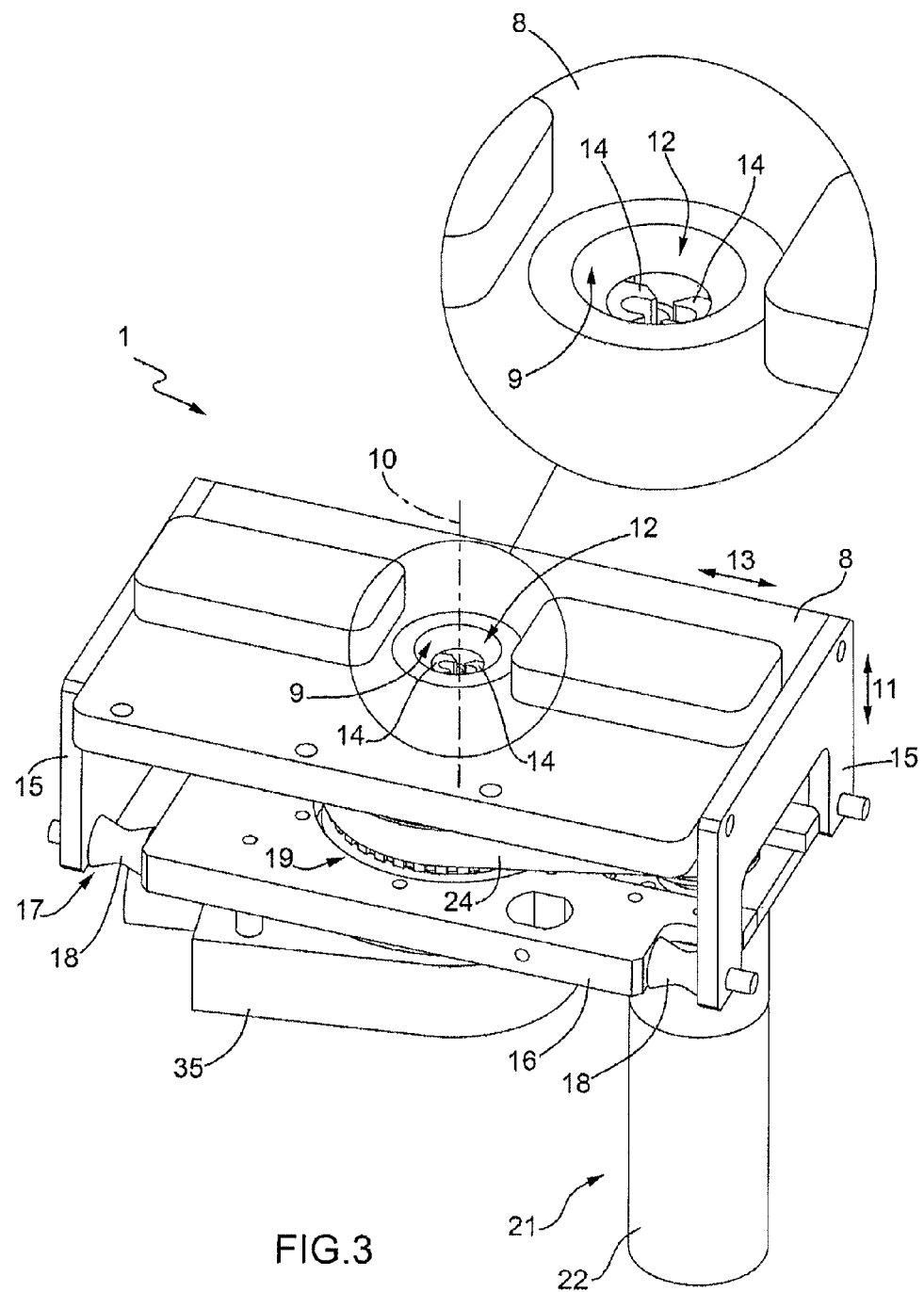
FIG. 3 is a second diagrammatic perspective view, with parts enlarged for clarity, of the apparatus in FIG. 1.

As shown in FIGS. 1 and 3, the apparatus 1 comprises a substantially horizontal upper support plate 8, which is fixed to a frame of an automatic machine for the preparation of pharmaceutical products (not shown), is provided with a central hole 9 having a substantially vertical longitudinal axis 10 parallel to a direction 11 and perpendicular to the plate 8, and supports a gripping device 12 of a syringe 3.

Device 12 comprises a pair of actuating cylinders (not shown), which are fixed to a lower face of the plate 8 from opposite sides of the axis 10 in a horizontal direction 13 transversal to direction 11, extend in direction 13 and have respective outlet rods each defining a respective jaw 14.

The jaws 14 are mobile in direction 13 between a clamping position and a release position of the cylinder 5 of a syringe 3.

The apparatus 1 further comprises two side plates 15, parallel to each other, which extend downwards from the plate 8 perpendicular to direction 13, and carry connected a lower, substantially horizontal support plate 16, which extends under the plate 8 perpendicular to direction 11 and is coupled in sliding manner to plates 15 by means of the interposition of a shock absorber device 17 for performing rectilinear movements in direction 11 itself with respect to the plate 8.

The device 17 comprises, in the case in point, four elastic elements 18 mounted between the plates 15 and 16 at the vertexes of the plate 16 itself.

Figure 4:
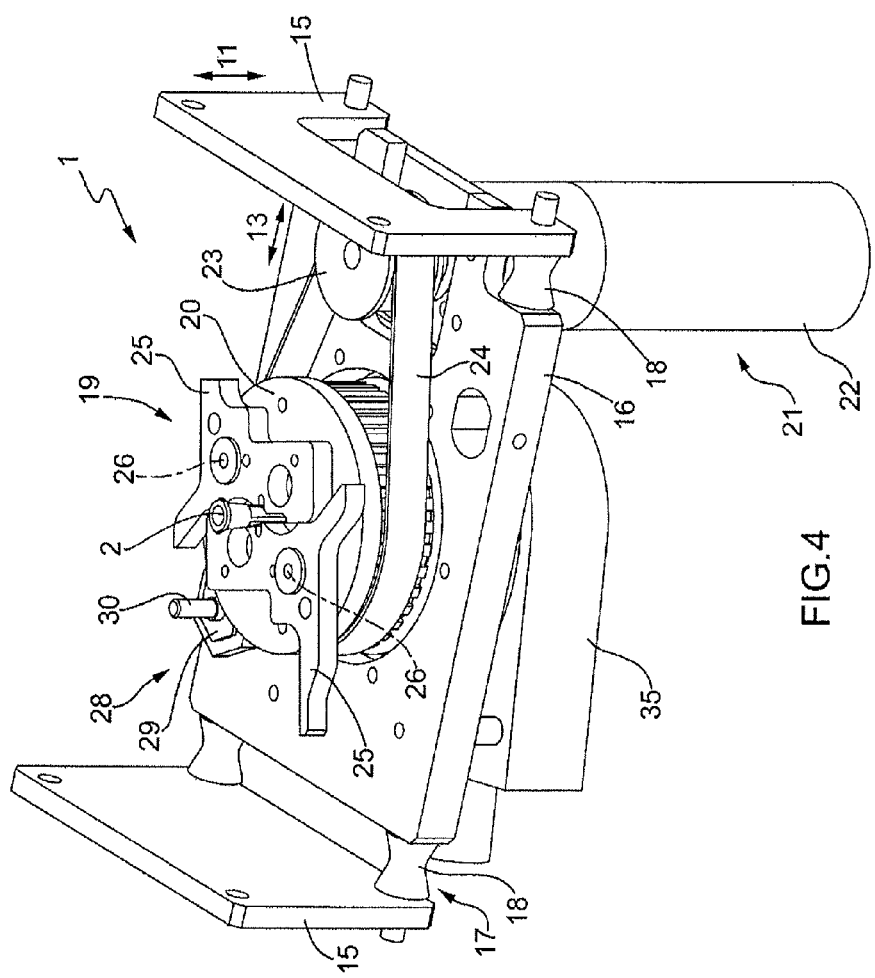
FIG. 4 is a diagrammatic view of a detail in FIGS. 1 and 3.
Figure 5:
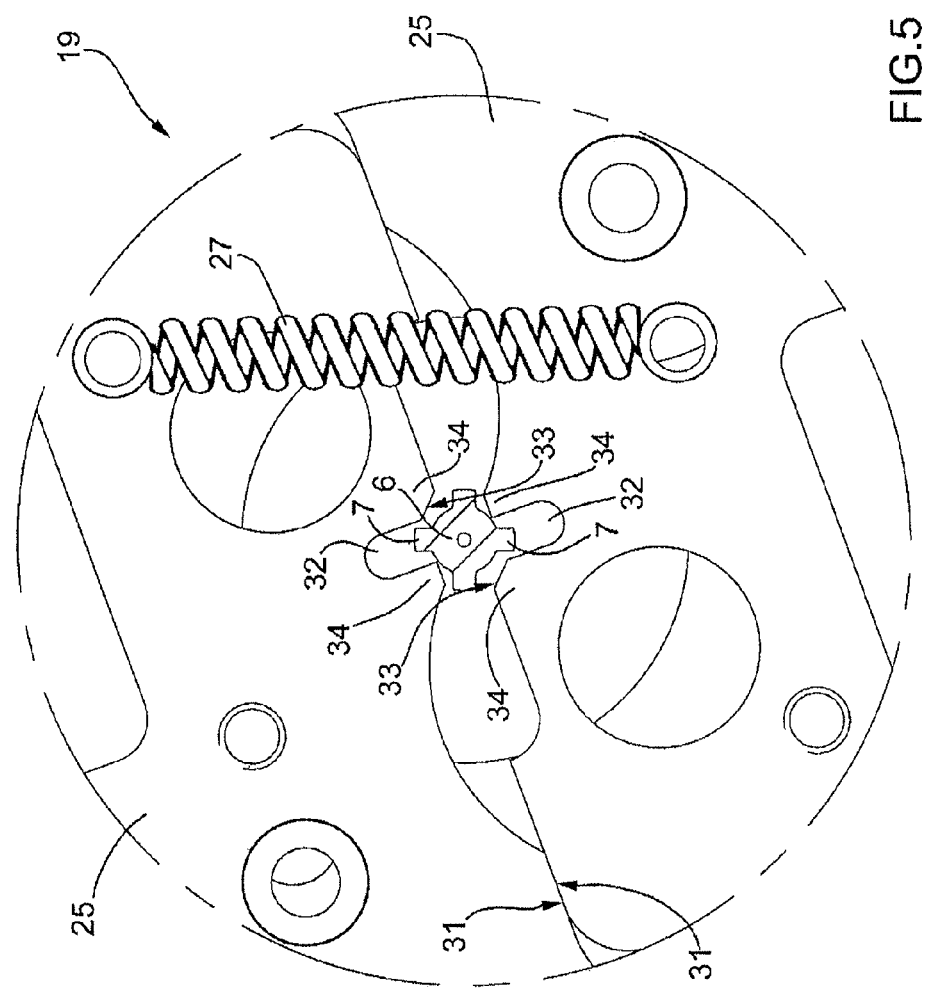
FIGS. 5 and 6 are two diagrammatic plan views of the detail in FIG. 4 shown in two different operating positions.
Figure 6:
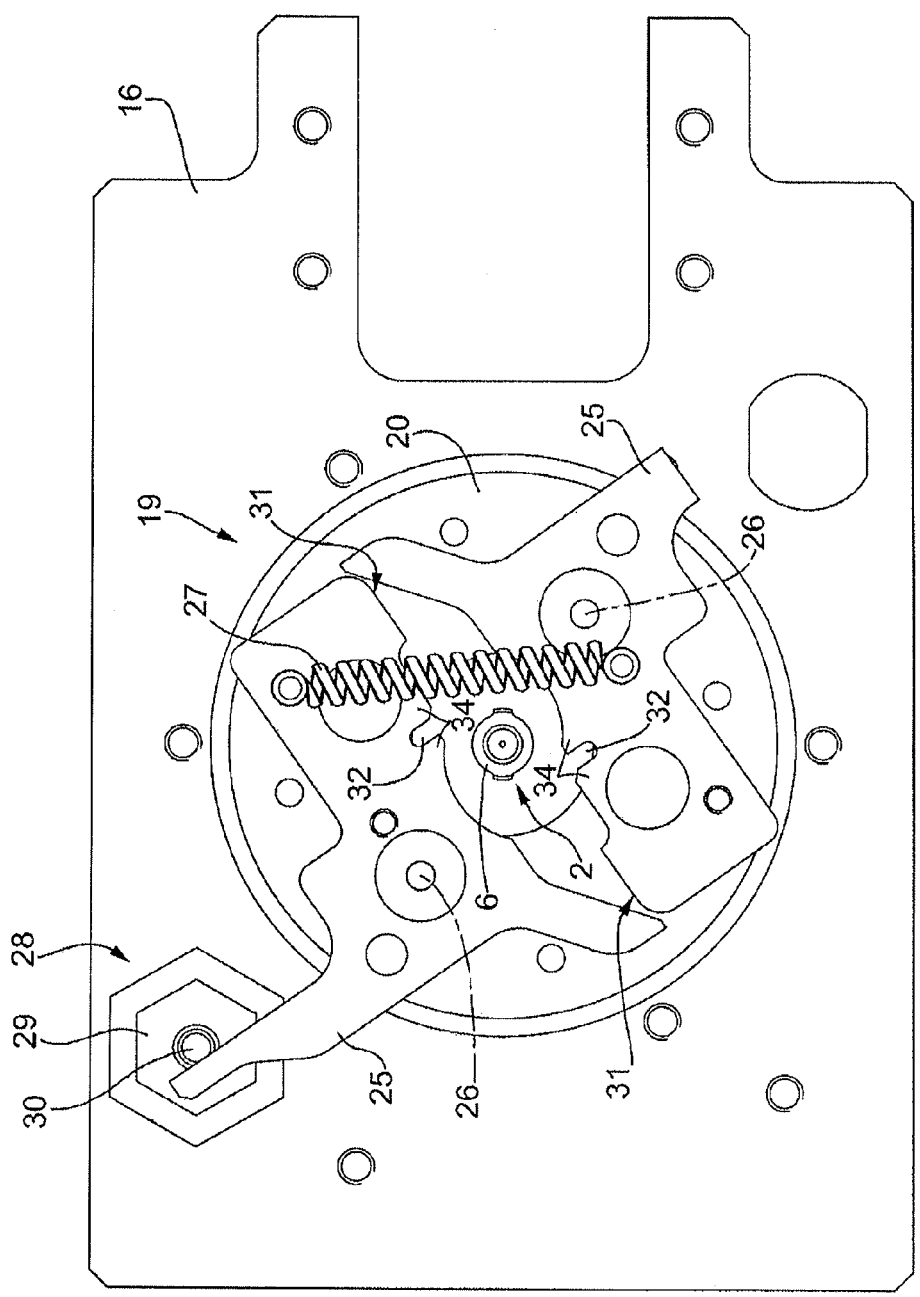

With reference to FIG. 4, the apparatus 1 is further provided with a gripping device 19 of a needle 2 comprising a disc 20, which is mounted on the plate 16 coaxially to axis 10, and is rotationally coupled to the plate 16 to turn with respect to the plate 16 and under the bias of an actuating device 21 about axis 10 itself (clockwise in FIGS. 5 and 6).

The device 21 comprises an electric motor 22, which is fixed to the plate 16, extends in direction 11, and has an output shaft 23 connected to the disc 20 by means of a belt transmission 24.

The device 19 further comprises two shaped jaws 25, which are rotationally coupled to disc 20 to turn, with respect to the disc 20 itself, about respective fulcrum axes 26 parallel to each other and to direction 11, and are moved, and normally kept, in a clamping position of a needle 2 (FIG. 5) by a spring 27 interposed between the jaws 25 themselves.

With regards to the above, it is worth specifying that the spring 27 is arranged so as to exert a tightening torque directed clockwise, and thus agreeing with the sense of rotation of the disc 20, on the jaws 25.

The jaws 25 are moved against the bias of the spring 27 from the clamping position to a release position of the needle 2 (FIG. 6) by an actuating device 28 comprising an actuating cylinder 29, which is fixed to the plate 16 parallel to direction 11, and has an outlet rod 30 movable between a lowered rest position (not shown), in which the rod 30 is arranged outside the conveying path of the jaws 25 about axis 10, and a raised operating position (FIGS. 4 and 6), in which the rod 30 is arranged within the conveying path of the jaws 25 about the axis 10 to intercept one of the jaws 25 themselves.

As shown in FIGS. 5 and 6, each jaw 25 is limited by an end face 31, which faces the other jaw 25, is arranged substantially in contact with the face 31 of the other jaw 24 following a movement of the jaws 25 to their clamping position, and has a slot 32, which is obtained through the jaw 25 parallel to direction 11, and is adapted to receive a projection 7.

The face 31 of each jaw 25 is further shaped so as to define, along with the other jaw 25 and when the jaws 25 are arranged in their clamping position, two further slots 33, which face each other and are adapted to each receive a respective projection 7.

Each slot 32 is laterally limited by two teeth 34, which are obtained on the face 31 of the respective jaw 25, and cooperate with the corresponding teeth 34 of the face 31 of the other jaw 25 to laterally limit the slots 33.

The apparatus 1 finally comprises a detection sensor 35 mounted under the plate 16 to detect the drop of the needle 2 removed from the syringe 3 and released from the jaws 25.

The operation of the apparatus 1 will now be described starting from an instant in which the jaws 14 are arranged in their release position, the outlet rod 30 of the actuating cylinder 29 is arranged in its raised operating position, and the disc 20 is turned about the axis 10 to engage one of the jaws 25 in the rod 30 and to move the jaws 25 to their release position.

After having inserted the syringe 3 through the hole 9 coaxially to the axis 10 (e.g. by means of a robotized arm), the jaws 14 are moved to their clamping position, the rod 30 is moved to its lowered rest position so as to disengage the jaw 25 and allow the jaws 25 to be arranged in their clamping position, and the disc 20 is turned about the axis 10 firstly to allow the projections 7 to correctly engage the slots 32, 33 and thus to unscrew the needle 2 from the syringe 3.

Once engaged in the respective slots 32, 33, the projections 7 exert on the jaws 25, during the rotation of the gripping device 19 about the axis 10, a tightening torque, which is oriented clockwise (i.e. in the same sense as the rotation of the disc 20) so as to lock the jaws 25 in their clamping position and to prevent the projections 7 from disengaging the respective slots 32, 33 due to the elasticity of the spring 27.

Since the syringe 3 is axially and angularly locked in the gripping device 12, the assembly defined by the plate 16 and by the gripping device 19 is moved downwards against the bias of the elastic elements 18 of the shock absorber device 17 during the unscrewing of the needle 2 of the syringe 3. In other words, the disc 20, the jaws 25 and the needle 2 are moved with a roto-translating movement about and along the mentioned axis 10 in order to unscrew the needle 2 from the syringe 3.

Once the needle 2 has been disengaged from the syringe 3, the jaws 14 are opened to disengage the syringe 3 of the apparatus 1; the rod 30 is moved again to its raised operating position to engage one of the jaws 25, move the jaws 25 to their release position, and allow the needle 2 to drop into a collection container (not shown) arranged under the plate 16; and the dropping of the needle 2 is detected by the sensor 35.

The invention claimed is:

1. An apparatus for the removal of needles (2) of syringes (3), each syringe (3) comprising a cylinder (5) provided with a threaded end, a plunger (4) engaged in a sliding manner in the cylinder (5), and a needle (2) screwed onto the threaded end of the cylinder (5); the apparatus comprising a first gripping device (19) comprising a pair of first jaws (25), which are mobile between a clamping position and a release position of a needle (2) of a syringe (3); and being characterized in that it comprises, furthermore, a second gripping device (12) of the syringe (3) and an actuating device (21) for moving the two gripping devices (19, 12) with respect to one another with a roto-translating movement around and along a longitudinal axis (10) of the syringe (3), so as to unscrew the needle (2) from the threaded end of the cylinder (5), wherein the second gripping device (12) comprises two second jaws (14) which are mobile between a clamping position and a release position of the syringe (3).

2. The apparatus according to claim 1, wherein the first gripping device (19) comprises, furthermore, first actuating means (27) for moving the first jaws (25) to their clamping position, and normally keeping them there, and second actuating means (28) for moving the first jaws (25) from the clamping position to the release position.

3. The apparatus according to claim 2, wherein the first actuating means (27) comprise at least one spring interposed between the two first jaws (25).

4. The apparatus according to claim 2, wherein the second actuating means (28) comprise at least one actuating member (30), which is mobile between a rest position, in which the actuating member (30) is arranged outside a conveying path of the first jaws (25) around said longitudinal axis (10), and an operating position, in which the actuating member (30) is arranged inside said conveying path, so as to intercept a said first jaw (25) and move it to said release position.

5. The apparatus according to claim 1, wherein the two gripping devices (19, 12) are coupled to each other in a sliding manner by means of the interposition of a shock absorber device (17), so as to move with respect to one another along said longitudinal axis (10).

6. The apparatus according to claim 1, wherein the needle (2) comprises a threaded hub (6), which is screwed onto the threaded end of the cylinder (5), and presents at least one projection (7) protruding towards the outside of the hub (6) itself; the first gripping device (19) comprising, for each projection (7), a respective slot (32, 33) obtained on the first jaws (25), so as to receive the projection (7) and angularly lock the needle (2) and the first jaws (25) themselves to each other.

7. The apparatus according to claim 6, wherein the needle (2) presents four projections (7) protruding towards the outside of the hub (6); each first jaw (25) being delimited by an end face (31), which faces the other first jaw (25), presents a said slot (32), and is shaped so as to define, with the end face (31) of the other first jaw (25), two said slots (33), when the first jaws (25) are arranged in their clamping position.

8. The apparatus according to claim 6, wherein the projections (7), when locked inside the respective slots (32, 33), exert on the first jaws (25), during the rotation of the first gripping device (19) around said longitudinal axis (10), a tightening torque which is oriented so as to lock the first jaws (25) themselves in their clamping position.

* * * * *